(12) United States Patent
Belef

(10) Patent No.: US 6,936,059 B2
(45) Date of Patent: Aug. 30, 2005

(54) ENDOVASCULAR GUIDEWIRE FILTER AND METHODS OF USE

(75) Inventor: W. Martin Belef, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 586 days.

(21) Appl. No.: 10/039,102

(22) Filed: Jan. 4, 2002

(65) Prior Publication Data
US 2002/0095171 A1 Jul. 18, 2002

Related U.S. Application Data

(60) Provisional application No. 60/262,135, filed on Jan. 16, 2001.

(51) Int. Cl.$^7$ .............................................. A61M 29/00
(52) U.S. Cl. ...................................................... 606/200
(58) Field of Search ................................ 606/113, 114, 606/127, 200, 159

(56) References Cited

U.S. PATENT DOCUMENTS

| | | |
|---|---|---|
| 3,472,230 A | 10/1969 | Fogarty |
| 3,952,747 A | 4/1976 | Kimmell, Jr. |
| 3,996,938 A | 12/1976 | Clark, III |
| 4,046,150 A * | 9/1977 | Schwartz et al. ............ 606/127 |
| 4,425,908 A | 1/1984 | Simon |
| 4,590,938 A | 5/1986 | Segura et al. |
| 4,619,246 A | 10/1986 | Molgaard-Nielsen et al. |
| 4,650,466 A | 3/1987 | Luther |
| 4,688,553 A | 8/1987 | Metals |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |

(Continued)

FOREIGN PATENT DOCUMENTS

| | | |
|---|---|---|
| DE | 28 21 048 | 7/1980 |
| DE | 34 17 738 | 11/1985 |
| DE | 40 30 998 A1 | 10/1990 |
| DE | 199 16 162 | 10/2000 |
| EP | 0 200 688 | 11/1986 |

(Continued)

OTHER PUBLICATIONS

"Atherosclerotic Disease of the Aortic Arch as a Risk Factor of Recurrent Ischemic Stroke," The New England Journal of Medicine, pp. 1216–1221 (May 1996).

(Continued)

Primary Examiner—Kevin T. Truong
(74) Attorney, Agent, or Firm—Crompton, Seager & Tufte LLC

(57) ABSTRACT

A filter device for temporary placement of a filter in an artery or vein is disclosed. The devices include (1) an elongate tubular member having a single or double side-wire loop, (2) an elongate member having a filter bonded to a circular rim joined by a plurality of tethers and an independently moveable tether, and (3) an elongate member having a parachute filter joined by a plurality of flexible struts. The filter conforms to the interior of a vessel wall when expanded and contracts to a consistent diameter without bunching when stowed. The filter devices may act as guidewires for guiding a therapeutic catheter to a region of interest within a vessel. Methods of using the filter device to entrap and remove embolic material from a vessel during endovascular procedures are also disclosed.

11 Claims, 12 Drawing Sheets

U.S. PATENT DOCUMENTS

| | | |
|---|---|---|
| 4,842,579 A | 6/1989 | Shiber |
| 4,873,978 A | 10/1989 | Ginsburg |
| 4,921,478 A | 5/1990 | Solano et al. |
| 4,921,484 A | 5/1990 | Hillstead |
| 4,926,858 A | 5/1990 | Gifford, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,192,286 A * | 3/1993 | Phan et al. .................. 606/127 |
| 5,224,953 A | 7/1993 | Morgentaler |
| 5,329,942 A | 7/1994 | Gunther et al. |
| 5,330,484 A | 7/1994 | Gunther |
| 5,354,310 A | 10/1994 | Garnie et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Bouewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,391,044 B1 * | 5/2002 | Yadav et al. ................. 606/200 |

FOREIGN PATENT DOCUMENTS

| | | |
|---|---|---|
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |

| | | |
|---|---|---|
| JP | 8-187294 A | 7/1996 |
| RU | SU 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01//67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Radiology Growth," *Cardiovascular* Device Update, 2(3):1–12 (Mar. 1996).

"Protruding Atheromas in the Thoracic Aortic and Systemic Embolization," pp. 423–427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR, 141*:601–604 (Sep. 1983).

Cragg, Andrew et al., "Nonsurgical Placement of Arterial Endoprosthesis: A New Technique Using Nitinol Wire," AJR, pp. 261–263 (Apr. 1983).

Diethrich et al., "Percutaneous Techniques for Endoluminal Carotid Interventions," *J.* Endovasc. Surg., 3:182–202 (1996).

Fadali, A. Moneim, "A filtering device for the prevention of particulate embolization during the course of cardiac surgery," Surgery, 64(3):634–639 (Sep. 1968).

Haissaguerre et al., "Spontaneous Initiation of Atrial Fibrillation by Ectopic Beats Originating in the Pulmonary Veins," *The New England Journal of Medicine*, *339*(10):659–666 (Sep. 1988).

Jordan, Jr. et al., "Microemboli Detected by Transcranial Doppler Monitoring . . . ," Cardiovascular Surgery, 7(1)33–38 (Jan. 1999).

Lesh, "Can Catheter Ablation Cure Atrial Fibrillation?" *ACC Current Journal Review*, pp. 38–40 (Sep./Oct. 1997).

Lund et al., "Long–Term Patentcy of Ductus Arteriosus After Balloon Dilation: an Experimental Study," Laboratory Investigation, 69(4):772–774 (Apr. 1984).

Marache et al., "Percutaneous Transluminal Venous Angioplasty . . . ," *American Heart Journal*, 125(2 Pt 1):362–366 (Feb. 1993).

Mazur et al., "Directional Atherectomy with the Omini-cath™: A Unique New Catheter System," Catheterization and Cardiovascular Diagnosis, 31:17–84 (1994).

Moussa, MD, Issaam "Stents Don't Require Systemic Anticoagulation . . . But the Technique (and Results) Must be Optimal," Journal of Invasive Cardiol., 8(E):3E–7E, (1996).

Nakanishi et al., "Catheter Intervention to Venous System Using Expandable Metallic Stents," Rinsho Kyobu Geka, 14(2):English Abstract Only (Apr. 1994).

Onal et al., "Primary Stenting for Complex Atherosclerotic Plaques in Aortic and Iliac Stenoses," Cardiovascular & Interventional Radiology, 21(5):386–392 (1998).

Theron et al., "New Triple Coaxial Catheter System for Carotid Angioplasty with Cerebral Protection," American Journal of Neuroradiology, 11:869–874 (1990).

Tunick et al., "Protruding atherosclerotic plaque in the aortic archo f patients with systemic embolization: A new finding seen by transesophageal echocardiography," *American Heart Journal* 120(3):658–660 (Sep. 1990).

Waksman et al., "Distal Embolization is Common After Directional Atherectomy . . . ," American Heart Journal, 129(3):430–435 (1995).

Wholey, Mark H. et al., PTA and Stents in the Treatment of Extracranial Circulation, *The Journal of Invasive Cardiology*, 8(E):25E–30E (1996).

* cited by examiner

ENDOVASCULAR GUIDEWIRE FILTER AND METHODS OF USE

This application hereby claims the benefit under Title 35, United States Code, §119(e) of U.S. Provisional Application Ser. No. 60/262,135 filed on Jan. 16, 2001.

FIELD OF THE INVENTION

The present invention relates generally to devices and methods for providing temporary placement of a filter in a blood vessel. More particularly, the invention provides a filter structure that conforms to the interior vessel wall with minimum gap and can be collapsed to facilitate its passage across large vascular lesions.

BACKGROUND OF THE INVENTION

Treatment of thrombotic or atherosclerotic lesions in blood vessels using an endovascular approach has recently proven to be an effective and reliable alternative to surgical intervention in selected patients. For example, directional atherectomy and percutaneous translumenal coronary angioplasty (PTCA) with or without stent deployment are useful in treating patients with coronary occlusion. Atherectomy physically removes plaque by cutting, pulverizing, or shaving in atherosclerotic arteries using a catheter-deliverable endarterectomy device. Angioplasty enlarges the lumenal diameter of a stenotic vessel by exerting mechanical force on the vascular walls. In addition to using angioplasty, stenting, and/or atherectomy on the coronary vasculature, these endovascular techniques have also proven useful in treating other vascular lesions in, for example, carotid artery stenosis, peripheral arterial occlusive disease (especially the aorta, the iliac artery, and the femoral artery), renal artery stenosis caused by atherosclerosis or fibromuscular disease, superior vena cava syndrome, and occlusive iliac vein thrombosis resistant to thrombolysis.

It is well recognized that one of the complications associated with endovascular techniques is the dislodgment of embolic materials generated during manipulation of the vessel, thereby causing occlusion of the narrower vessels downstream and ischemia or infarct of the organ which the vessel supplies. In 1995, Waksman et al. disclosed that distal embolization is common after directional atherectomy in coronary arteries and saphenous vein grafts. See Waksman et al., American Heart Journal 129(3):430–5 (1995), incorporated herein by reference in its entirety. This study found that distal embolization occurs in 28% (31 out of 111) of the patients undergoing atherectomy. In January 1999, Jordan, Jr. et al. disclosed that treatment of carotid stenosis using percutaneous angioplasty with stenting is associated with more than eight times the rate of microemboli seen using carotid endarterectomy. See Jordan, Jr. et al., Cardiovascular surgery 7(1): 33–8 (1999), incorporated herein by reference in its entirety. Microemboli, as detected by transcranial Doppler monitoring in this study, have been shown to be a potential cause of stroke. The embolic materials include calcium, intimal debris, atheromatous plaque, thrombi, and/ or air.

Filters mounted to the distal end of guidewires have been proposed for entrapment of vascular emboli. A majority of these devices includes a filter which is attached to a guidewire and is mechanically actuated via struts or a pre-shaped basket which deploys in the vessel. These filters are typically mesh "parachutes" which are attached to the shaft of the wire at the distal end, and to wire struts which extend outward in a radial direction at their proximal end. The radial struts open the proximal end of the filter to the wall of the vessel. Blood flowing through the vessel is forced through the mesh thereby capturing embolic material in the filter. These devices are self-directing and can be placed intravascularly.

However, there are several disadvantages associated with guidewire-filtration. First, the steerability of the guidewire may be altered as compared to conventional guidewires due to the size of the filter, and the guidewire may bend, kink, and/or loop around in the vessel, making insertion of the filter through a complex vascular lesion difficult. Secondly, the current filter designs, e.g., a basket or net, often fail to conform to the internal perimeter of the vessel, and distal embolization can still occur despite the filter placement. Thirdly, as the filter is stowed, the filter material is gathered together with "bunching" of the material at the perimeter, causing uncontrolled gathering and creating relatively large and poorly defined crossing profiles. As a result, the current filter designs require large capture sheaths to deploy and stow the filter.

What is needed are simple and safe blood filtering devices that conform to a patient's vessel wall to prevent distal embolization during endovascular procedures, and provide easy steerability and a controlled closure profile when contracted. Existing devices are inadequate for this purpose.

SUMMARY OF THE INVENTION

The present invention provides devices and methods that protect a patient from distal embolization during endovascular procedures, e.g., atherectomy, angioplasty, or stent-deployment. More specifically, endovascular filters that conform to the interior vessel wall with minimum gap are disclosed for capturing embolic material generated during a procedure in an artery or vein.

In one embodiment, the filter device includes a first elongate member having a proximal end and a distal end. The first elongate member is typically a tubular member having first and second proximal ports locate a short distance proximal (1–3 cm, preferably 1 cm) from the distal end. The first port will generally be located approximately 180° circumferentially from the second port. One or two flexible members, e.g., wires made of stainless steel or plastic, each of which has a proximal end that extends through one of the first or second proximal ports on the first elongate member, and a distal end that is attached to the first elongate member at a position distal of the port.

In certain embodiments the distal end of one or both flexible members passes through first and second distal ports. Thus, the distal end of each flexible member is attached to the first elongate member within a lumenal wall of the first elongate member after passing through the distal port. The first proximal port on the tubular member is located at a circumferential position approximately 180° from the second proximal port, and the first distal port on the tubular member is located at a circumferential position approximately 180° from the second distal port. The first flexible member passes through one proximal port, and then through the distal port that is 180° from the proximal port through which the flexible member passes, and the same for the second flexible member. A filter is disposed about the first and second flexible members, which are operable between an expanded condition and a contracted condition from the proximal end of the tubular member. In certain embodiments, the filter is bonded at an edge to the first and the second flexible members.

In some embodiments, the filter comprises a mesh as described in Tsugita et al., U.S. Pat. No. 5,911,734, incorporated herein by reference in its entirety. In other embodiments, the filter is made of a biocompatible material, such as plastic (e.g., kynar, polyethylene tetrachloride, polyethylene, or mylar), having pores that are precision machined by laser, etching, and/or chemical milling to provide less traumatic pathways for blood flow. Anticoagulants, such as heparin and heparinoids, may be applied to the filter to reduce thrombi formation.

In another embodiment, the device comprises first and second elongate members. The second elongate member is slideably disposed within a lumen of the first elongate member. The proximal ends of the first and second flexible members are fixed to the second elongate member, and the distal ends of the flexible members are fixed to the first elongate member. The flexible members are operated by sliding the second elongate member distally within the first elongate member, thereby advancing the flexible members through the proximal ports and placing the filter in an expanded state.

In another embodiment, the filter device includes a flexible loop having a first end, a second end, and an intermediate section positioned near a distal port of the elongate tubular member. A filter is disposed about the intermediate section. The first end is operated to advance the flexible loop distally. The intermediate section of the loop extends through the distal port and into a lumen of a vessel for deployment of the filter. In some embodiments, a tether, which is attached at one end to the intermediate section of the loop, restrains the intermediate section and changes the orientation of a plane described by the loop, preferably orienting the plane perpendicular to the axis of the vessel.

In another embodiment, a plurality of tethers are coupled at a first end to the distal end of the elongate member, and the second end of each of the tethers is coupled to the edge of a parachute filter. In certain embodiments the edge of the filter is mounted about a circular rim. An independently moveable tether is also coupled to the filter edge or the circular rim and is operable at a proximal end. A capture sheath, slideably disposed over the filter and the circular rim, assists in stowing the filter and prevents accidental dislodgment of embolic material during filter closure. The circular rim or filter edge can be rotated into alignment substantially parallel with the elongate member and capture sheath by withdrawing proximally the independently moveable tether. In some embodiments, the circular rim is constructed of a superelastic material, e.g., nitinol. This alignment enables the capture sheath to cover the filter and circular rim to assist with removal of the filter from the vessel.

In another embodiment, the filter is attached to the elongate member by a plurality of flexible struts. Each of the flexible struts is coupled at a first end to the distal end of the elongate member and coupled at a second end to the filter. The filter is contracted by rotating the elongate member, which in turn winds the flexible struts. A capture sheath is disposed about the elongate member and the filter for stowage of the filter. As the flexible struts wind, the filter is closed, and the capture sheath is able to cover the flexible struts and filter to assist in removal from the vessel.

The filter devices of the present invention are most useful in capturing embolic debris generated during endovascular procedures within a coronary artery, aorta, common carotid artery, external and internal carotid arteries, brachiocephalic trunk, middle cerebral artery, basilar artery, vertebral artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery, and all other arteries carrying oxygenated blood. The filter devices are also useful in preventing distal embolization in the venous circulation, including the superior vena cava, inferior vena cava, external and internal jugular veins, brachiocephalic vein, pulmonary artery, subclavian vein, brachial vein, axillary vein, iliac vein, renal vein, femoral vein, profunda femoris vein, great saphenous vein, portal vein, splenic vein, hepatic vein, and azygous vein.

In a first method of using the filter device having first and second flexible members, the filter is placed in a contracted state. The distal end of the tubular member is inserted percutaneously through an artery or vein and advanced into or beyond a region of interest, typically a stenotic lesion caused by buildup of atherosclerotic plaque and/or thrombi. The filter is then expanded downstream of the vascular occlusion by operating the first and second flexible members. In this way, the filter structure conforms to the interior vessel wall with minimum gap, as the elongate tubular member lies against the luminal wall of the vessel. The elongate tubular member then acts as a platform, or guidewire, to guide therapeutic instruments to operate on the stenosis within the region of interest. After the stenotic lesion is removed by endovascular procedure(s), e.g., angioplasty, atherectomy, or stent deployment, the filter is collapsed and removed from the vessel, together with the captured embolic debris. When the filter is stowed, the flexible members are tightened against the tubular member and constricted by a capture sheath advanced distally over the filter during closure, creating a controlled closure of the filter. In this way, bunching of the filter and undesired release of the captured embolic debris are avoided.

In another method, using the filter device having a flexible loop, the distal end of the elongate tubular member is positioned at a region of interest within a patient's vessel. The first end of the loop is advanced distally, advancing the intermediate section through the distal port until the filter covers the lumen of the vessel. The elongate tubular member is then used to guide therapeutic catheters to operate on the stenosis at the region of interest.

In another method, using the parachute filter device with or without a circular rim coupled to the elongate member by a plurality of tethers, the distal end of the elongate member is first positioned within a region of interest. The capture sheath is withdrawn to release the circular rim and filter within the region of interest. Therapeutic catheters are then deployed upstream the filter. To stow the filter, the independently moveable tether is withdrawn to rotate the circular rim so that a plane defined by the circular rim or mouth of the filter is parallel to a line defined by the elongate member, thereby bringing the rim into alignment with the elongate member and capture sheath. The capture sheath is then advanced over the circular rim and filter, wherein the mouth of the filter and/or the circular rim collapses to a substantially oval shape.

In another method, using the filter device having a filter coupled to the elongate member by a plurality of flexible struts, the distal end of the elongate member is advanced to a region of interest within a patient's vessel. The capture sheath is withdrawn to release the filter, thereby expanding the filter within the region of interest. After completion of endovascular procedures, the elongate member is rotated, thereby winding the plurality of flexible struts to contract the filter. The capture sheath is advanced distally to cover the wound flexible struts and the filter, thereby providing tight stowage of the filter and preventing accidental release of captured emboli.

It will be understood that there are several advantages to using the filter devices and methods disclosed herein for capturing and removing embolic debris during endovascular procedures. For example, the filter devices (1) are particularly well suited for temporary filtration of blood in any vessel to entrap embolic debris, thereby minimizing neurologic, cognitive, and cardiac complications associated with distal embolization, (2) conform to the interior vessel wall with minimum gap, (3) can be collapsed to a uniform and predictable size, (4) can be delivered over a guidewire as a rapid exchange device, (5) can be delivered through a lumen of an angioplasty or stent deployment device, (6) may include an atraumatic distal tip to minimize vessel wall injury, (7) enable an operator to steer and deploy the filter without kinking, bending, and/or looping of the catheter because of the small size ratio of filter to catheter, (8) can pass a large occluding lesion due to their small diameter when collapsed, (9) can be used as a guidewire over which a therapeutic catheter may be advanced, and (10) can be used in adult and pediatric patients.

BRIEF DESCRIPTION OF THE DRAWINGS

FIG. 1D depicts the filter device of FIG. 1C fully expanded.

FIG. 1E depicts an end view of the filter device of FIG. 1D.

DETAILED DESCRIPTION

Figure 1A:
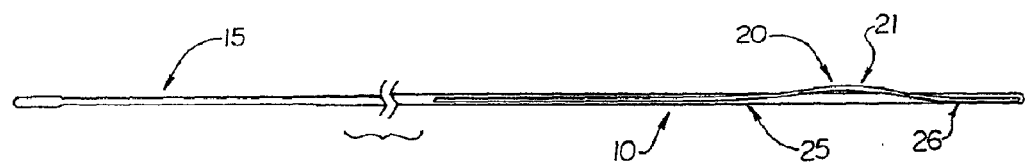
FIG. 1A depicts an embodiment of a filter device having a double side-wire loop.

A filter device for temporary placement in a vessel, either an artery or vein, is provided as depicted in FIGS. 1A through 1H. FIG. 1A shows elongate tubular member 10 having proximal ports 25 and distal ports 26 located at a distal region. Proximal ports 25 are located circumferentially approximately 180° from each other. Distal ports 25 are also located circumferentially approximately 180° from each other. The circumferential positioning, however, may vary between 90° and 270°, more preferably 100° to 260°, more preferably 110° to 250°, more preferably 120° to 240°, more preferably 130° to 230°, more preferably 140° to 220°, more preferably 150° to 210°, more preferably 160° to 200°, more preferably 170° to 190°, most preferably approximately 180°.

A first flexible member 20 passes through port 25 at a proximal end, crosses 180° over elongate member 10 at point 21, and either is coupled externally at the distal end of elongate member 10 (not shown), or passes through distal port 26 and is coupled to the luminal wall at the interior of elongate member 10. It will be understood that first flexible member 20 passes through proximal port 25 on one side of elongate member 10, and passes through distal port 26 on the opposite side of the elongate member.

Figure 1B:
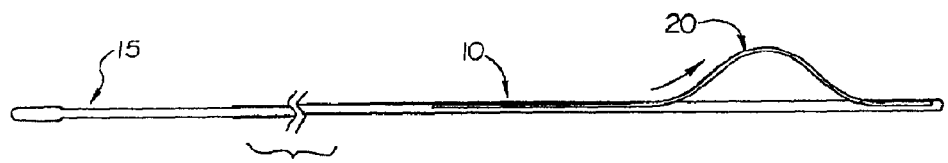
FIG. 1B depicts the filter device of FIG. 1A partially expanded.
Figure 1C:
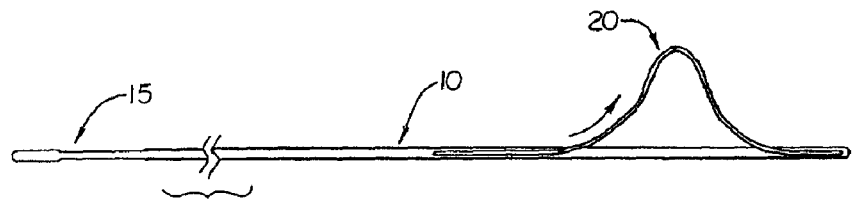
FIG. 1C depicts the filter device of FIG. 1B further expanded.
Figure 1C:
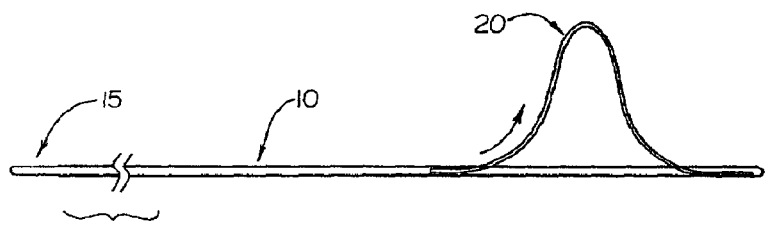
Figure 1C:
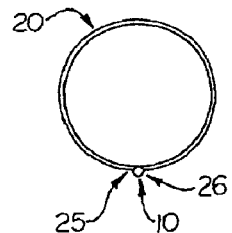
Figure 1F:
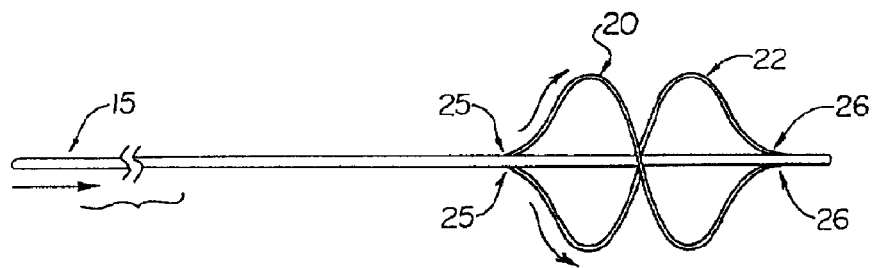
FIG. 1F depicts an top view of the filter device of FIG. 1D.

One flexible member or two flexible members may be used. FIGS. 1A to 1H depict the use of two flexible members 20 and 22. As shown in FIG. 1F, the second flexible member 22 passes through a second port 25 at a proximal end, crosses 180° over elongate member 10 in a direction opposite to that of first flexible member 20, and either is coupled externally at the distal end of elongate member 10 (not shown), or passes through a second distal port 26 and is coupled to the luminal wall at the interior of elongate member 10. It will be understood that second flexible member 22 passes through a second proximal port 25 on one side of elongate member 10, and passes through a second distal port 26 on the opposite side of the elongate member.

First and second flexible members 20 and 22 may extend to the proximal end of elongate tubular member 10, or may be attached to the distal end of elongate member 15 which is slideably disposed within the lumen of tubular member 10, as depicted in FIG. 1A. When elongate member 15 is advanced distally as shown in FIGS. 1B, 1C, and 1D, flexible members 20 and 22 advance through proximal ports 25 to progressively enlarge loops extending radially about tubular member 10. FIG. 1E shows an end view of tubular member 10 and flexible member 20 extending from a proximal port 25 and through a distal port 26, and defining a circle that includes tubular member 10.

Figure 1G:
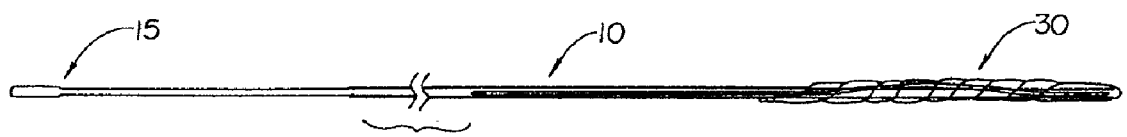
FIG. 1G depicts a collapsed filter mounted on the filter device of FIG. 1A.
Figure 1H:
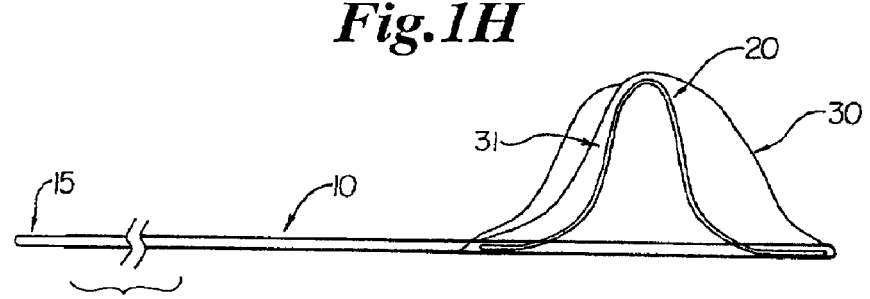
FIG. 1H depicts the filter of FIG. 1G expanded by operation of first and second side-wire loops.

FIG. 1F shows a top view of elongate tubular member 10, elongate member 15, and the double side-wire loop structure defined by first and second flexible member 20 and 22. FIG. 1G depicts filter structure 30 disposed about the side-wire loop structure before expansion. FIG. 1H shows an expanded side-wire loop structure having filter 30 disposed thereon, the filter having opening 31 that receives blood flow and emboli, and allows passage of blood but retains emboli in the filter. The filter may comprise a mesh material or a thin film with laser cut holes. The construction and use of a filter mesh have been thoroughly discussed in earlier applications including Barbut et al., U.S. application Ser. No. 08/533,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. Pat. No. 5,769,816, Barbut et al., U.S. application Ser. No. 08/645,762, filed May 14, 1996, and, Barbut et al., U.S. Pat. No. 5,662,671, and the contents of each of these prior disclosures are expressly incorporated herein by reference in their entirety.

Where a thin film with laser cut holes is used, the thin film will include any biocompatible material, such as plastic (e.g., kynar, polyethylene tetrachloride, polyethylene, or mylar). The processing used to create pores in the thin film can be either laser or chemical etching, stamping, or cutting by hand. The pores are precision machined into the filter material, thereby providing less traumatic pathways for blood flow and minimizing activation of the intravascular clotting process. Anticoagulants, such as heparin and heparinoids, may be applied to the thin film to reduce thrombi formation. In the embodiments of the filter devices that are to be used in the aorta, pore size is 500 $\mu$m or less, more preferably 400 $\mu$m or less, more preferably 300 $\mu$m or less, more preferably 200 $\mu$m or less, more preferably 100 $\mu$m or less, more preferably 50 $\mu$m or less and usually larger than at least a red blood cell. Typical dimensions include pore size of 20–500 $\mu$m, and a petal thickness of 0.0005–0.003 inches.

Figure 2:
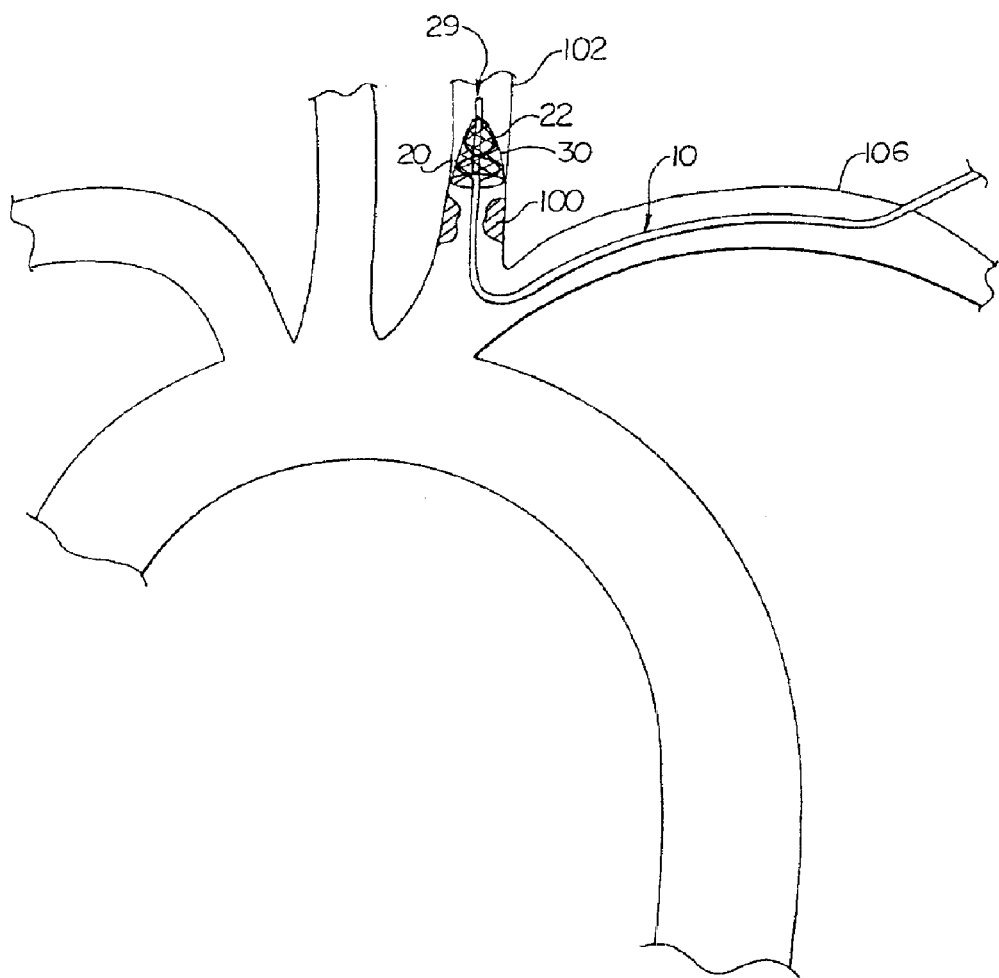
FIG. 2 depicts the filter device of FIG. 1H deployed in the left common carotid artery.

FIG. 2 shows the double side-wire loop filter of FIG. 1A through 1H deployed within left common carotid artery 102. Elongate tubular member 10 is advanced to position through left subclavian artery 106. Tubular member 10 includes atraumatic tip 29 at a distal end to reduce vessel trauma and better navigate tight stenotic lesion 100. Filter 30 expands about flexible members 20 and 22 within the lumen of left common carotid artery 102 to capture dislodged embolic material, e.g., calcium, atheromatous plaque, thrombi, air, and vascular debris.

Figure 3A:
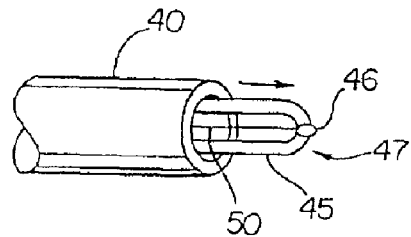
FIG. 3A depicts an embodiment of a filter device having an expandable flexible loop.
Figure 3B:
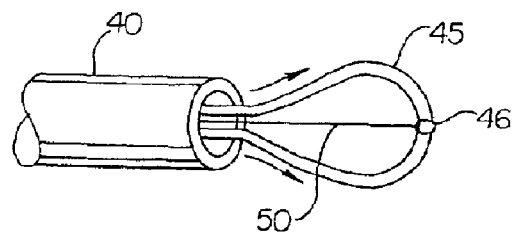
FIG. 3B depicts the filter device of FIG. 3A partially expanded.
Figure 3C:
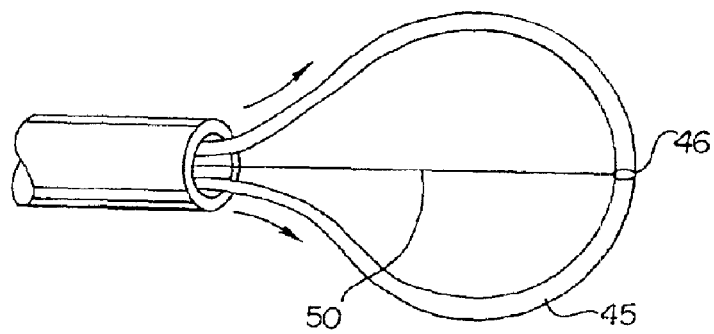
FIG. 3C depicts the filter device of FIG. 3B fully expanded.

FIGS. 3A through 3F depict another embodiment of a filter device. Elongate tubular member 40 contains a loop of wire or other flexible material 45 within its lumen. Wire 45 has a first end, a second end, and intermediate region 47 shown in FIG. 3A. Optional tether 50 is joined to intermediate section 47 at position 46. A filter (not shown for clarity) is attached to the intermediate section of the wire loop and contained within the lumen of tubular member 40 before deployment. The first and/or second end of flexible loop 45 is advanced distally, causing intermediate section 47 to extend through the distal port on tubular member 40 into the lumen of the vessel, as shown in FIGS. 3B and 3C.

Figure 3D:
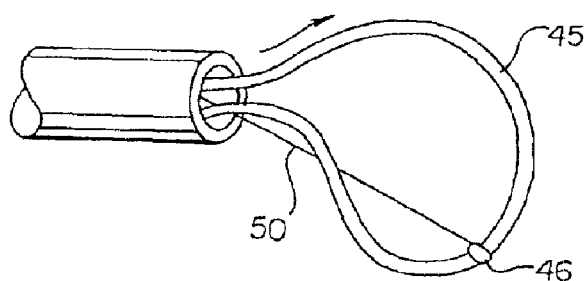
FIG. 3D depicts the filter device of FIG. 3C expanded with adjusted orientation.
Figure 3E:
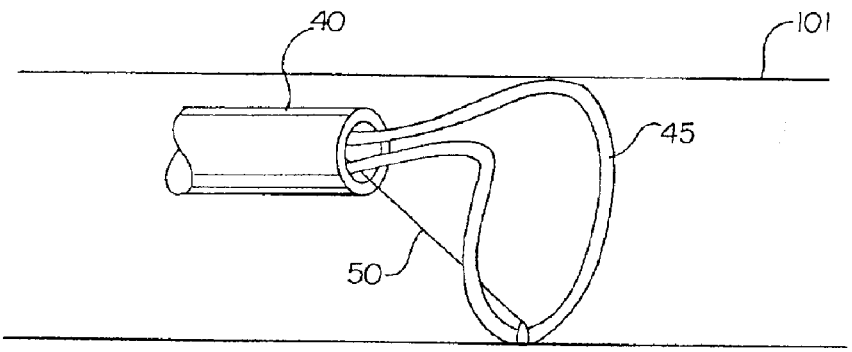
FIG. 3E depicts the filter device of FIG. 3D disposed within a vessel.
Figure 3F:
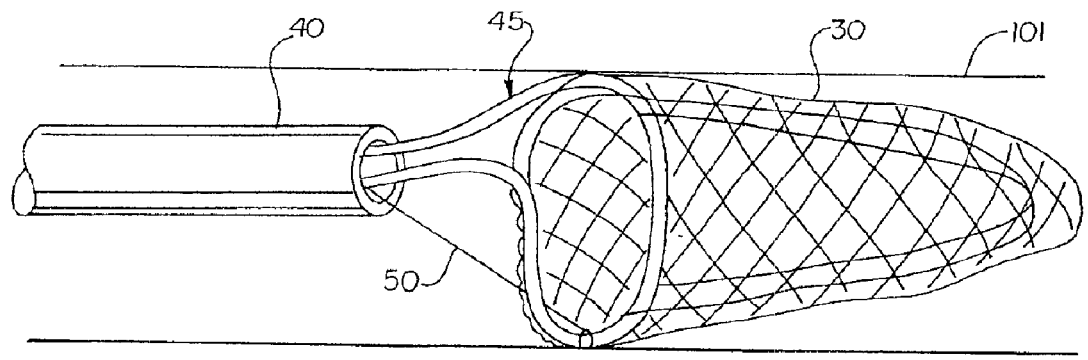
FIG. 3F depicts a filter device disposed about the flexible loop of FIG. 3E.

As loop 45 is advanced distally out of its containment lumen, it grows in diameter. The flexible loop (along with attached filter) continues to grow until it nears the diameter of the vessel in which the filter is being deployed. At this point, tether 50 restrains wire loop 45, and is operated independently as shown in FIG. 3D to change the orientation of the plane described by the loop. The plane of loop 45 is substantially parallel to the axis of tubular member 40 shown in FIG. 3C, but with operation of tether 50 as shown in FIG. 3E, the plane described by the loop is substantially perpendicular to the longitudinal axis of tubular member 40 and vessel 101. FIG. 3F shows final deployment of wire loop 45 and filter 30 within vessel 101. Loop 45 describes a plane that is substantially perpendicular to the longitudinal axis of the vessel, and the loop has reached a diameter such that the loop is in complete or nearly complete contact with the luminal wall of the vessel, thus forcing all or nearly all blood to flow through the filter material.

According to this embodiment, tubular member 40 may be constructed of a diameter of 0.04 inches, including the filter contained within the lumen, so that it can be delivered through a guidewire lumen of a percutaneous transluminal angioplasty balloon or stent delivery catheter. This device may also be configured so that the distal tip of tubular member 40 has a diameter of approximately 0.035 inches (or larger) to allow for ease of packaging of the filter and its wire loop within the containment lumen. The entire device would include a distal filter containment tip of tubular member 40 having a 0.035 inch outer diameter (OD) with an attached 0.014 inch diameter wire extending proximally from the tip. In use, the 0.014 inch diameter segment would be covered by a removable sheath having 0.035 inch OD. After delivery and deployment of the filter, the sheath is removed, leaving the 0.014 inch diameter wire in place, and holding the filter. the 0.014 inch diameter wire is then used to facilitate treatment of the vessel by advancing over the wire standard therapeutic over the wire catheter devices.

The wire loop can be made (preformed) of shape memory alloys, such as nitinol, and may be designed so that the tether is not needed to achieve proper orientation for filter deployment. The loop may alternatively be made of plastic or any other material that would facilitate deployment of the filter, so that the lumen of the vessel is completely covered by the filter and all blood flows through the filter.

Retraction and removal of the filter may be accomplished by reversing the process of deployment, or by use of a separate, and typically a larger diameter capture sheath the capture sheath is advanced over the 0.014 inch diameter segment of the filter device, the filter withdrawn proximally into the distal end of the capture sheath, and both devices are removed together.

Figure 4B:
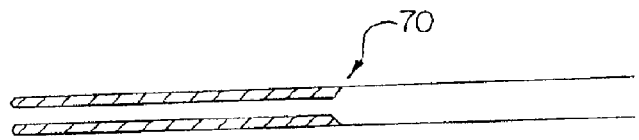
FIG. 4B depicts a capture sheath.
Figure 4A:
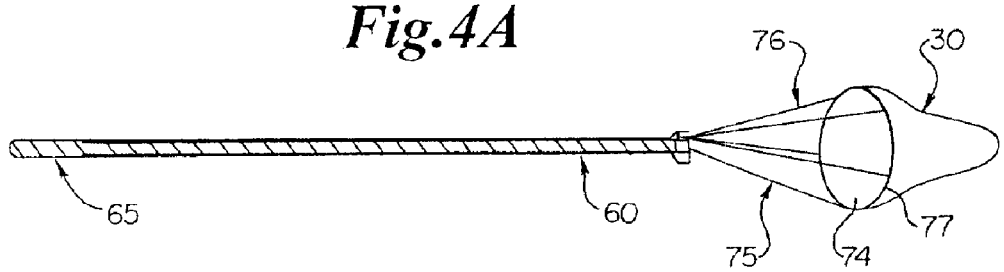
FIG. 4A depicts an embodiment of a filter device having an independently moveable tether.

FIGS. 4A through 4J depict the design, deployment, use, and retrieval of an alternative filter device for capturing debris that flow downstream from an interventional site in a patient's vessel. FIG. 4A shows filter 30 which takes on a substantially conical shape and is designed so that its opening, or mouth 74, can expand to completely or nearly completely fills the lumen of a vessel. The filter extends distally from mouth 74 of the filter and provides an area where debris is trapped. The mouth of filter 30 may, in certain embodiment, include circular rim 77 which is a frame comprised of a bendable material, preferably a plastic or superelastic material, e.g., nitinol. Filter 30 is held in position within a vessel by means of a plurality of tethers 76, wherein the number of tethers are two or more, more preferably three or more. An independently operable tether 75 is also attached to rim 77. The tethers are attached at equidistant points around the mouth of the filter. Tethers 76 extend proximally and are attached to elongate tubular member 60. The tethers are of substantially equal lengths, such that the plane described by the mouth of the filter is maintained in a position substantially perpendicular to the longitudinal axis of the vessel. Second elongate member 65 is slideably disposed within elongate tubular member 60, and is attached to independently moveable tether 75 at a distal end of member 65. Tubular member 60 is sized to permit typically therapeutic and diagnostic devices to be delivered over the filter guidewire while the filter is deployed at a distal end.

As shown in FIG. 4B, during delivery and removal of the filter to and from its deployment site, capture sheath 70 is used to contain filter 30 to prevent it from catching and injuring the vessel wall during movement, and to retain and remove from the patient debris captured by the filter. Once the filter is at the region of interest, it is pushed from the distal end of capture sheath 70. To retrieve the filter, it is pulled back into capture sheath 70 and removed from the patient. Alternatively, separate delivery and retrieval sheaths may be used. For example, where a large amount of debris is collected by the filter, a larger diameter retrieval sheath may be required.

FIG. 4B shows filter 30 and tethers 76 folded and packaged within the containment area at the distal end of delivery sheath 70 and ready for deployment within a region of interest a patient's vessel. In certain embodiments, the distal end 66 of tubular member 60 is larger in diameter than the body of tubular member 60 and acts as a plunger that is used to push the filter out of the containment area at the distal end of sheath 70. FIG. 4D shows sheath 70 being pulled proximally relative to tubular member 60, thereby causing the filter to be ejected from the distal end of sheath 70. The filter begins to expand as it leaves the sheath. Alternatively, tubular member 60 may be pushed distally relative to sheath 70 to cause ejection of filter 30.

Figure 4C:
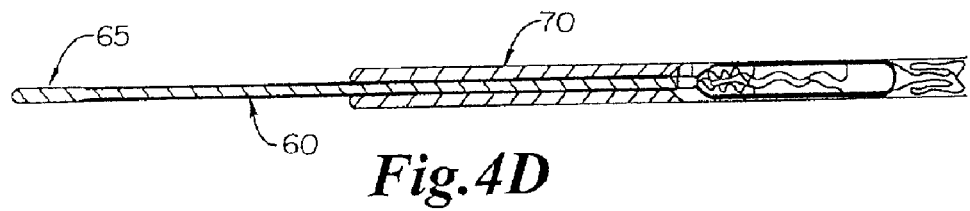
FIG. 4C depicts the capture sheath of FIG. 4B covering the filter of FIG. 4A.
Figure 4D:
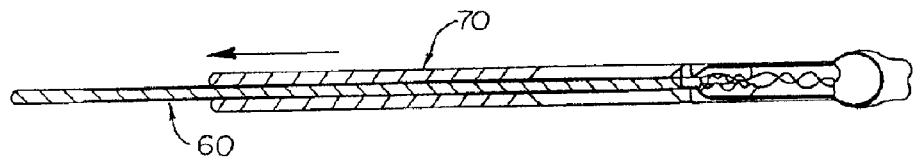
FIG. 4D depicts partial removal of the capture sheath of FIG. 4C.
Figure 4E:
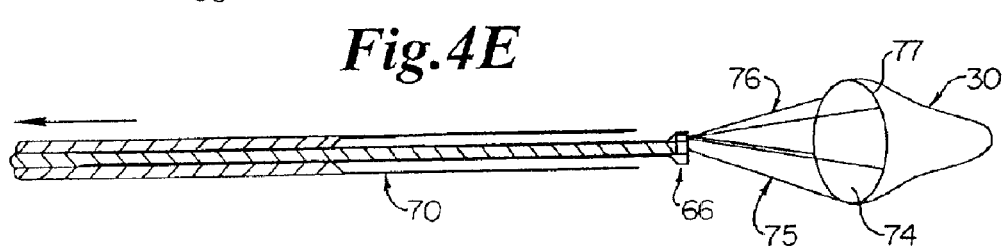
FIG. 4E depicts further removal of the capture sheath of FIG. 4D.
Figure 4F:
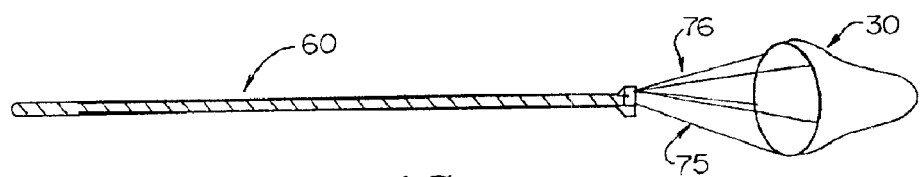
FIG. 4F depicts complete removal of the capture sheath of FIG. 4E.

FIG. 4E shows the filter fully ejected from sheath 70 and deployed. Filter mouth 74 completely or nearly completely fills the lumen of the vessel in which it is deployed. Circular rim 77, when use, aids in full expansion of the filter. FIG. 4F shows complete removal of sheath 70 from tubular member 60 so that member 60 can act as a guidewire and is ready to receive and provide support and guidance for other therapeutic devices that are to be delivered to the area of interest within the vessel.

Figure 4G:
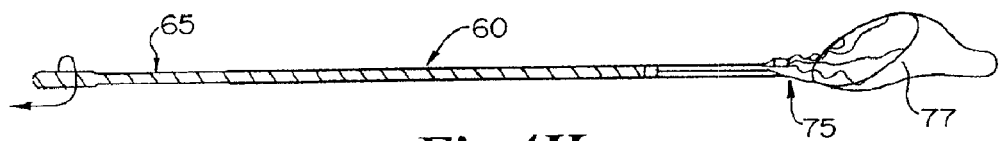
FIG. 4G depicts operation of the independently moveable tether to reorient the circular rim.
Figure 4H:
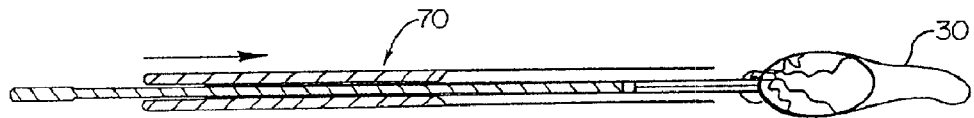
FIG. 4H depicts advancement of the capture sheath over the elongate member of FIG. 4G.
Figure 4I:
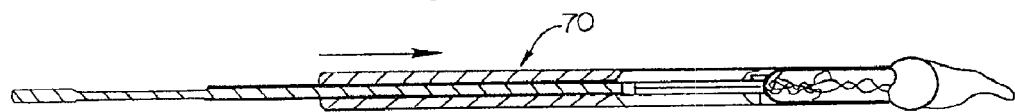
FIG. 4I depicts further advancement of the capture sheath to partially cover the circular rim of FIG. 4H.
Figure 4J:
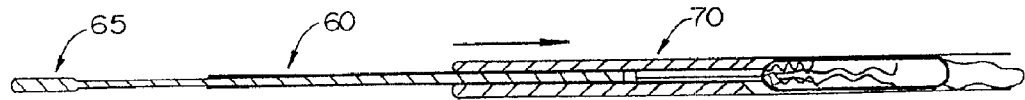
FIG. 4J depicts complete coverage of the circular rim by the capture sheath of FIG. 4I.

FIG. 4G shows the beginning of filter retrieval process. Elongate member 65 is retracted proximally relatively to tubular member 60. Independently moveable tether 75 attached to elongate member 65 is thereby pulled proximally, and this action tilts the mouth of the filter from its fully deployed position and readies it to be pulled into capture sheath 70. Just prior to retrieval, the plane described by the mouth of the filter is positioned substantially parallel to the longitudinal axis of the vessel. FIG. 4H shows capture sheath 70 delivered over tubular member 60 and ready to be further advanced to cover filter 30 and the debris it contains. FIG. 4I shows capture sheath 70 advancing and capturing filter 30. As filter 30 enters sheath 70, the filter mouth folds upon itself in much the same manner as it was loaded into sheath 70 before deployment. Alternatively, once the distal end of sheath 70 has advanced to the filter, tubular member 60 and elongate member 65 may be pulled proximally relative to sheath 70, thus pulling the filter inside the distal end of sheath 70. FIG. 4J shows filter 30 fully retracted inside the distal end of capture sheath 70. The entire filter system can then be removed from the patient.

Figure 5A:
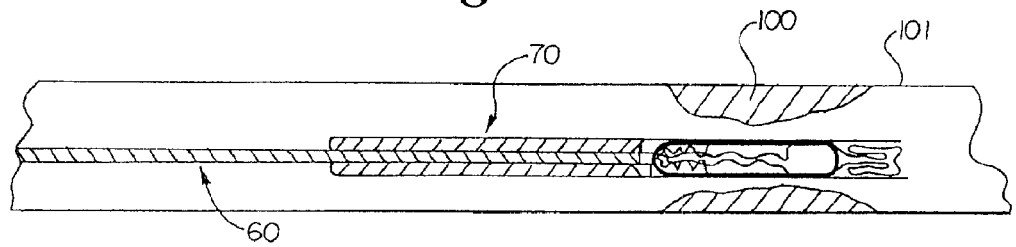
FIG. 5A depicts the filter device of FIG. 4C inserted within a stenotic region of a vessel.
Figure 5B:
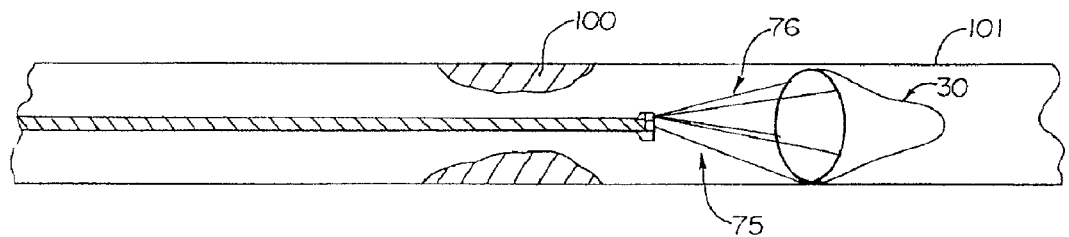
FIG. 5B depicts the filter device of FIG. 5A deployed downstream of the stenotic region.
Figure 5C:
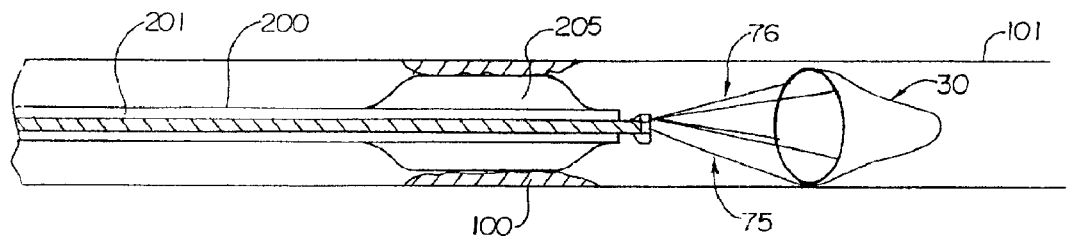
FIG. 5C depicts an angioplasty catheter advanced over the filter device of FIG. 5B.
Figure 5D:
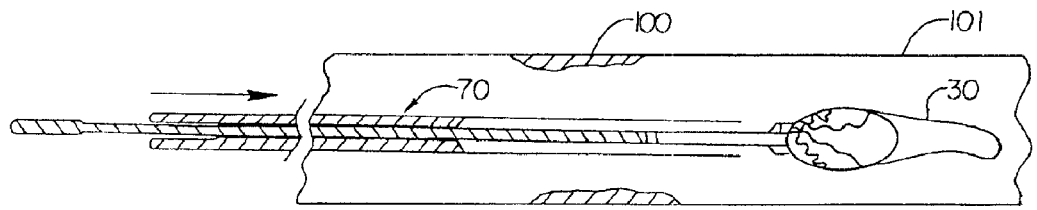
FIG. 5D depicts retrieval of the filter device of FIG. 5C using a capture sheath.

FIG. 5A depicts the filter device of FIG. 4C inserted within stenotic lesion 100 of vessel 101. FIG. 5B shows the filter device of FIG. 5A after deployment of filter 30 downstream stenotic lesion 100. After removal of capture sheath 70, tubular member 60 serves as a guidewire for delivering a therapeutic catheter, such as angioplasty catheter 200, as shown in FIG. 5C. Angioplasty catheter 200 includes balloon 205 in a distal region thereof, and carries tubular member 60 within guidewire lumen 210. Atherectomy and stent deployment catheters may alternatively be used in place of or in addition of the angioplasty catheter depicted in FIG. 5C. After inflation of angioplasty balloon 205 to compress stenotic lesion 100, the balloon is deflated and the angioplasty catheter 200 is removed from the patient's vessel. Capture sheath 70 is then advanced along tubular member 60 to retrieve filter 30 as shown in FIG. 5D.

Figure 6A:
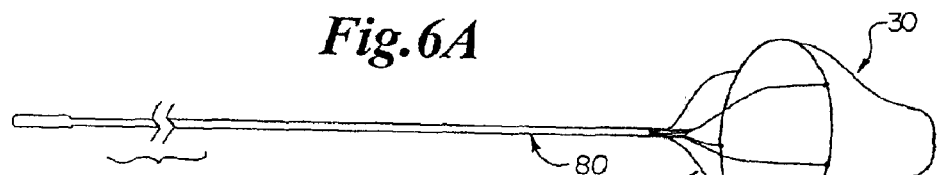
FIG. 6A depicts an embodiment of a filter device having a parachute filter coupled by flexible struts to an elongate member.
Figure 6B:
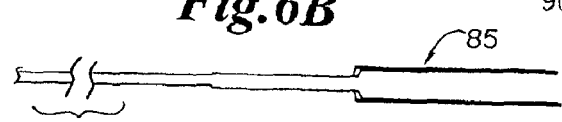
FIG. 6B depicts a capture sheath.

FIGS. 6A through 6I depict the design, deployment, use, and retrieval of another filter device for capturing debris that flow downstream from an interventional site in a patient's vessel. FIG. 6A shows the main components of the filter and delivery system, while FIG. 6B shows the capture sheath. Filter 30 in FIG. 6A is substantially conical and designed so that its opening, or mouth 91, expands to completely or nearly completely fill the lumen of a vessel. The filter material then extends distally (downstream) from the mouth of the filter and provides an area where debris is captured. Filter 30 is held in position in a vessel by flexible struts 90 attached at equidistant point around the mouth of the filter. The flexible struts extend proximally to elongate member 80 to which the struts are attached. A minimum of three flexible struts is needed, while five flexible struts are shown in FIG. 6A.

Struts 90 may be constructed of a superelastic material, preferably a shape memory material, such as nitinol. Struts 90 are preformed and attached to elongate member 80 so that when the struts are advanced distally and freed from containment sheath 85. The struts then expand outward to open mouth 91 of filter 30, so that the filter substantially fills the vessel in which it is deployed. The struts are of substantially equal lengths so that the plane described by the mouth of filter 30 is maintained in a position substantially perpendicular to the longitudinal axis of the vessel. Struts 90 may also be taper ground in any number of ways so that struts 90 are smaller at their distal ends and can more easily conform to the vessel wall.

Surrounding elongate member 80 is capture sheath 85. The majority of the length of sheath 85, from its proximal end to near its distal end, has a diameter adapted to pass other interventional devices after the filter has been deployed. As such, sheath 85 may also serve as a guide wire. During delivery and removal of filter to and from its deployment site, sheath 85 contains filter 30 to prevent it from catching or injuring the vessel wall, and to retain and remove from the patient debris captured within the filter. When filter 30 reaches a region of interest, filter 30 is pushed distally from the distal end of capture sheath 85. To retrieve filter 30, the filter is pulled proximally into sheath 85, or sheath 85 is advanced over filter 30, and the combination is removed from the patient.

Figure 6C:
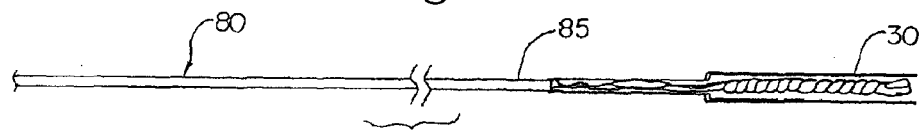
FIG. 6C depicts the capture sheath of FIG. 6B covering the filter of FIG. 6A.

FIG. 6C shows filter 30 and struts 90 packaged within the containment area at the distal end of capture sheath 85. As shown, filter 30 is ready for deployment. The distal end of sheath 85 has a larger diameter than elongate member 80 to provide adequate space for storage of struts 90, filter 30, and debris captured within filter 30.

Figure 6D:
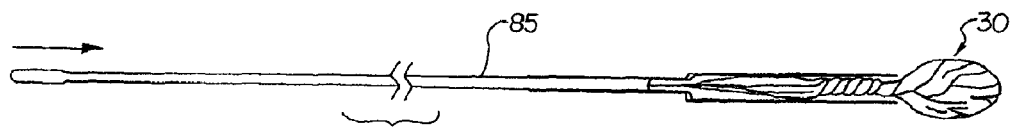
FIG. 6D depicts partial removal of the capture sheath of FIG. 6C.

FIG. 6D shows elongate member 80 being pushed distally relative to sheath 85, which causes filter 30 to be ejected from the distal end of sheath 85. Slight rotation of elongate member 80 during deployment may assist with deployment. Filter 30 begins to expand as it leaves sheath 85. Alternatively, sheath 85 may be pulled proximally relatively to elongate member 80 to release filter 30.

Figure 6E:
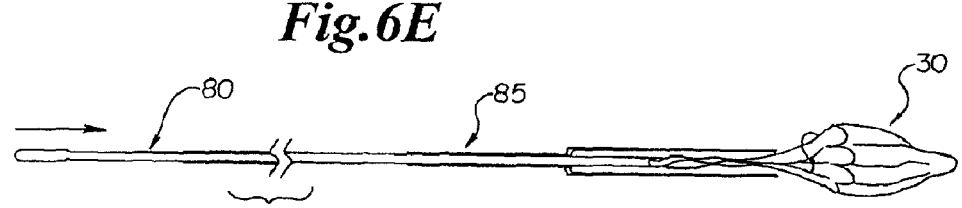
FIG. 6E depicts further removal of the capture sheath of FIG. 6D.
Figure 6F:
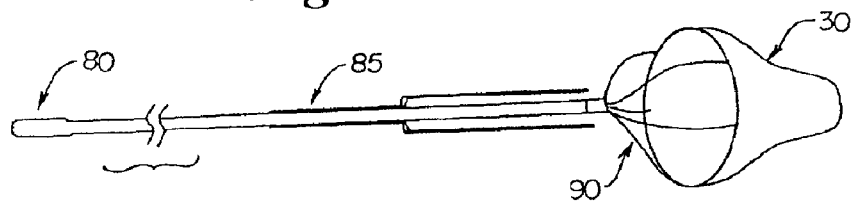
FIG. 6F depicts full expansion of the parachute filter of FIG. 6E.

FIG. 6E shows filter 30 fully ejected from sheath 85. Preformed struts 90 are beginning to leave sheath 85 and are expanding outward to open mouth 91 of filter 30. FIG. 6F shows struts 90 completely free of sheath 85 and fully expanding filter 30. Sheath 85 is now ready to function as a guidewire to receive and provide support for any other device, including therapeutic catheters, which are to be delivered to the region of interest.

Figure 6G:
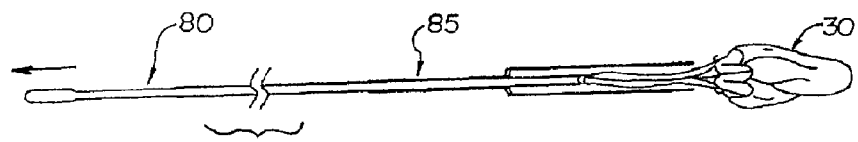
FIG. 6G depicts advancement of the capture sheath over the flexible struts of FIG. 6F.
Figure 6H:
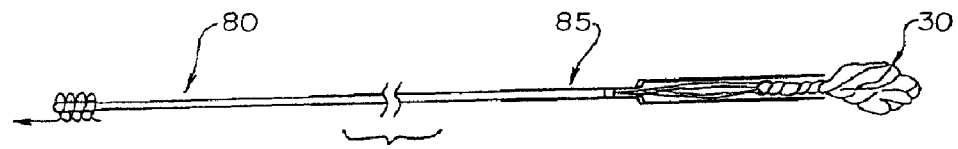
FIG. 6H depicts rotation of the elongate member and winding of the flexible struts of FIG. 6G.
Figure 6I:
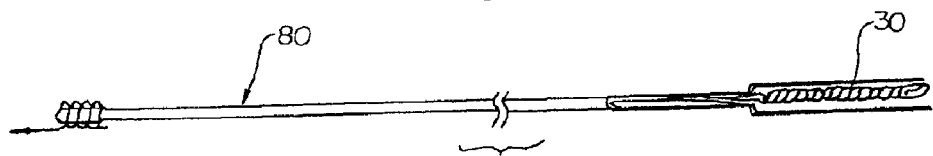
FIG. 6I depicts complete coverage of the wound flexible struts and filter of FIG. 6H.

FIG. 6G shows the beginning of the filter retrieval process. Elongate member 80 is pulled proximally relative to sheath 85, and this action causes struts 90 to begin collapsing as they enter the containment area at the distal end of sheath 85. The filter mouth begins to close, trapping debris inside filter 30. FIG. 6H shows struts 90 completely withdrawn sheath 85. As filter 30 begins to enter sheath 85, elongate member 80 is rotated as it is pulled proximally. This twisting action winds filter 30 and compacts the filter, which assists re-entering sheath 85. FIG. 6I shows filter 30 retracted inside the distal end of sheath 85. Filter 30 has been twisted and compacted into its containment area. The entire filter system can now be removed from the patient's vessel.

Figure 7A:
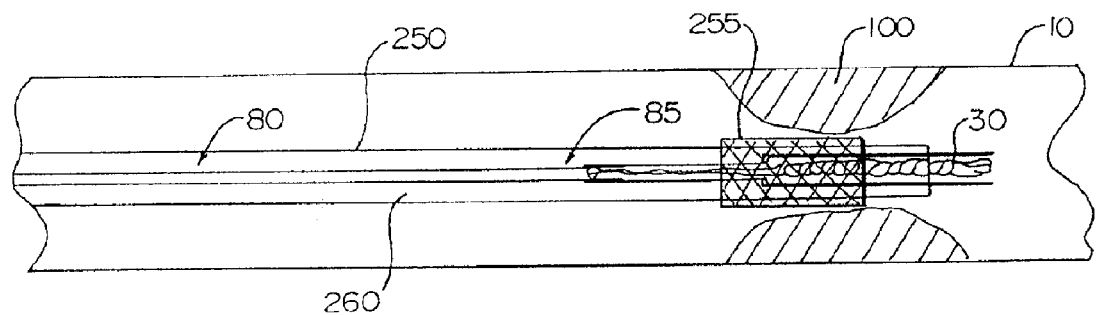
FIG. 7A depicts the filter device of FIG. 6C inserted through a lumen of a therapeutic catheter deployed within a stenotic lesion of a vessel.
Figure 7B:
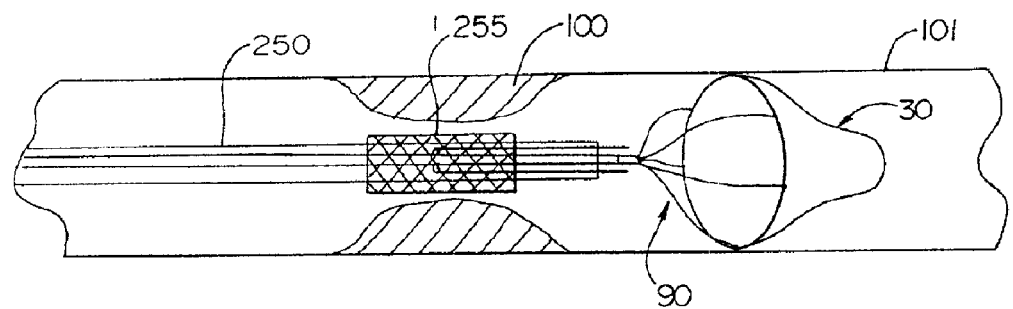
FIG. 7B depicts the filter device of FIG. 7A deployed downstream of the stenotic region.
Figure 7C:
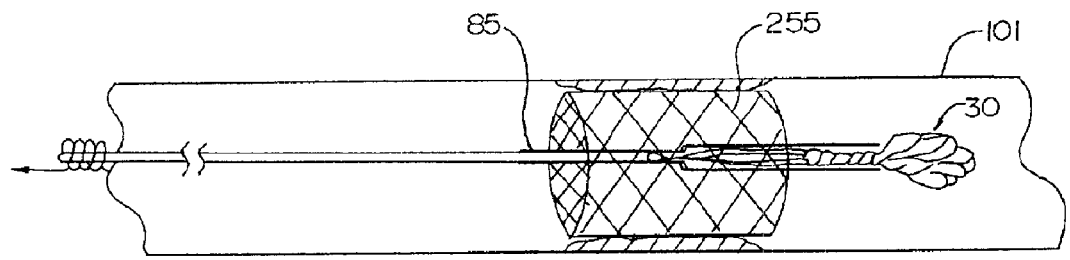
FIG. 7C depicts closure of the flexible struts and filter by winding of the struts and advancement of the capture sheath.

The filtration devices described herein can be used not only as guidewires to receive and provide support for any other device, but may also be advanced through the guidewire lumen of a therapeutic catheter once in place. For example, a conventional guidewire may be positioned within a vessel crossing a region of interest. A therapeutic catheter is then advanced over the conventional guidewire so that the therapeutic instrument lies within the region of interest. The conventional guidewire is then withdrawn, and a guidewire filter as described herein is advanced through the guidewire lumen of the therapeutic catheter. FIG. 7A, for example, shows stent deployment catheter 250 having stent 255 disposed on a distal region, and positioned across stenotic lesion 100 of vessel 101. The stent can be either self expanding or deployed by the action of a dilatation balloon. A filter guidewire as shown in FIG. 6C is advanced through guidewire lumen 260 of catheter 250 until filter 30 passes distally beyond catheter 250 and downstream of lesion 100. Sheath 85 is withdrawn and filter 30 is deployed within vessel 101 as shown in FIG. 7B. Stent 255 is then expanded to increase the luminal diameter across lesion 100, and catheter 250 is withdrawn from the vessel as shown in FIG. 7C. The filter is then captured by sheath 85 as described in FIG. 6H, and the filter guidewire is removed from the patient's vessel. Alternatively, therapeutic catheter 250, sheath 85, and filter 30 may be simultaneously removed after stent deployment.

Figure 8:
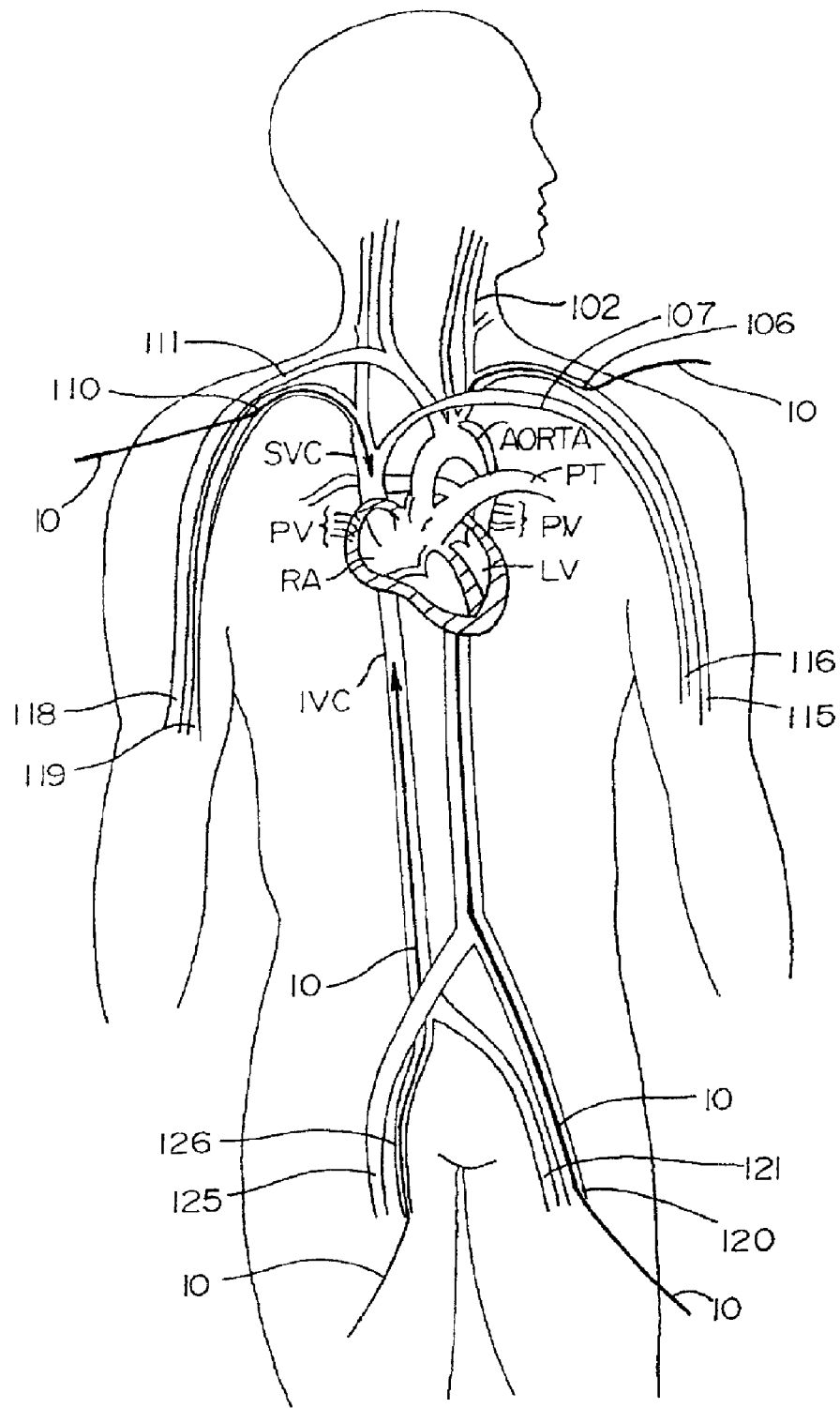
FIG. 8 depicts various percutaneous insertion sites for the filter devices described herein.

Various percutaneous insertion sites for the filter devices disclosed herein are depicted in FIG. 8. The filter device can be inserted through an incision on right subclavian artery 111, left subclavian artery 106, right brachial artery 118, left brachial artery 115, right femoral artery 125, or left femoral artery 120 to enter a patient's arterial circulation. The double side-wire loop filter of FIG. 1H having elongate tubular member 10 is shown inserted through left subclavian artery 106 or left femoral artery 120 and deployed within left common carotid artery 102. The filter device can also be inserted through an incision on right subclavian vein 110, left subclavian vein 107, right cubital vein 119, left cubital vein 116, right femoral vein 126, or left femoral vein 121 to enter a patient's venous circulation. The double side-wire loop filter of FIG. 1H is shown inserted through right subclavian vein 110 and deployed within the superior vena cava. The double side-wire loop filter of FIG. 1H is also shown inserted through right femoral vein 126 and deployed within the inferior vena cava.

The length of the elongate member which typically will serve as a guidewire is generally between 30 and 300 centimeters, preferably approximately between 50 and 180 centimeters. The outer diameter of the guidewire will generally be between 0.01 and 0.05 inches, preferably approximately between 0.014 and 0.035 inches. The filter will be capable of expanding to an outer diameter of at least 0.2 centimeters, more preferably at least 0.5 centimeters, more preferably at least 1.0 centimeters, more preferably at least 1.5 centimeters, more preferably at least 2.0 centimeters, more preferably at least 2.5 centimeters, more preferably at least 3.0 centimeters, more preferably at least 3.5 centimeters, more preferably at least 4.0 centimeters, more preferably at least 4.5 centimeters, more preferably at least 5.0 centimeters. The filter will be capable of contracting to an outer diameter of between 0.05 and 2.0 millimeters, preferably approximately between 0.8 and 1.2 millimeters. The outer diameter of the capture sheath will generally be between 0.5 and 2.2 millimeters, preferably approximately between 0.9 and 1.9 millimeters. These ranges cover suitable diameters for both pediatric and adult use. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. Moreover, it will be understood that each and every feature described for any given embodiment or in any reference incorporated herein, can be combined with any of the other embodiments described herein.

What is claimed is:

1. An endovascular filter, comprising:
   an elongate tubular member having a proximal end, a distal end, and a first proximal port proximal the distal end of the elongate tubular member;
   a first flexible member having a proximal end that passes through the first proximal port of the elongate tubular member, and having a distal end fixed to the elongate tubular member at a first point distal the first proximal port, the first point being located at a circumferential position approximately 180° from the first proximal port;

a filter disposed about the first flexible member, wherein the first flexible member is expanded by advancing distally the proximal end of the first flexible member.

2. The filter of claim 1, wherein the elongate tubular member has a second proximal port proximal the distal end of the elongate tubular member and located at a circumferential position approximately 180° from the first proximal port, and wherein the endovascular filter further comprises a second flexible member having a proximal end that passes through the second proximal port of the elongate tubular member, and having a distal end fixed to the elongate tubular member at a second point distal the second proximal port, the second point being located at a circumferential position approximately 180° from the second proximal port.

3. The filter of claim 2, further comprising an elongate member slideably disposed relative to the elongate tubular member, wherein the proximal ends of the first and second flexible members are fixed to the elongate member.

4. The filter of claim 1, wherein the filter comprises a mesh.

5. The filter of claim 3, wherein the first and second flexible members are expanded by sliding the elongate member distally.

6. The filter of claim 1, further comprising a capture sheath slideably disposed about the mesh.

7. The filter of claim 3, wherein the elongate member is disposed within a lumen of the elongate tubular member.

8. The filter of claim 1, wherein the filter is bonded at an edge to the first flexible member.

9. The filter of claim 1, wherein the filter comprises a thin film having laser cut holes.

10. The filter of claim 1, wherein the first flexible member passes through a first distal port and is attached within a lumen of the elongate tubular member, and wherein the first distal port is located at a circumferential position approximately 180 ° from the first proximal port.

11. The filter of claim 2, wherein the first flexible member passes through a first distal port and is attached within a lumen of the elongate tubular member, and wherein the first distal port is located at a circumferential position approximately 180° from the first proximal port, and wherein the second flexible member passes through a second distal port and is attached within a lumen of the elongate tubular member, and wherein the second distal port is located at a circumferential position approximately 180° from the second proximal port.

* * * * *